United States Patent [19]

Radford et al.

[11] Patent Number: 5,029,580

[45] Date of Patent: Jul. 9, 1991

[54] MEDICAL ASPIRATING APPARATUS WITH MULTI-LUMEN CATHETER TUBE AND METHODS

[75] Inventors: F. Richard Radford, Auburn, Wash.; Richard C. Lambert, Highland; Darrel Palmer, Sandy, both of Utah

[73] Assignee: Ballard Medical Products, Draper, Utah

[21] Appl. No.: 555,119

[22] Filed: Jul. 18, 1990

[51] Int. Cl.$^5$ .......................................... A61M 16/00
[52] U.S. Cl. ......................... 128/207.14; 128/202.16; 604/43; 604/19; 604/264
[58] Field of Search ...................... 128/207.14, 207.16, 128/202.16, 205.19, 207.18, 207.15; 604/43, 95, 96, 99, 19, 264

[56] References Cited

U.S. PATENT DOCUMENTS

| | | | |
|---|---|---|---|
| 1,944,553 | 1/1934 | Freund | 128/229 |
| 2,568,566 | 9/1951 | Sokolik | 128/240 |
| 2,912,982 | 11/1959 | Barsky | 128/912 |
| 3,322,126 | 5/1967 | Rüsch et al. | 128/351 |
| 3,363,629 | 1/1968 | Kuhn | 604/281 |
| 3,628,532 | 12/1971 | Magrath | 128/145.8 |
| 3,794,026 | 2/1974 | Jacobs | 128/207.15 X |
| 3,911,919 | 10/1975 | Raitte | 128/276 |
| 4,015,336 | 4/1977 | Johnson | 32/33 |
| 4,022,219 | 5/1977 | Basta | 128/351 |
| 4,027,659 | 6/1977 | Slingluff | 604/280 |
| 4,036,210 | 7/1977 | Campbell et al. | 128/2 F |
| 4,081,176 | 3/1978 | Johnson | 251/342 |
| 4,119,101 | 10/1978 | Igich | 128/207.15 |
| 4,193,406 | 3/1980 | Jinotti | 128/204.18 |
| 4,240,417 | 12/1980 | Holever | 128/912 |

(List continued on next page.)

FOREIGN PATENT DOCUMENTS

| | | |
|---|---|---|
| 241457 | 10/1974 | Australia . |
| 112668 | 7/1984 | European Pat. Off. . |
| 245607 | 3/1987 | Fed. Rep. of Germany . |
| 820182 | 11/1981 | Sweden . |
| 810245 | 7/1981 | U.S.S.R. . |
| WO810267 | 10/1981 | World Int. Prop. O. . |

OTHER PUBLICATIONS

"Side Eye Position", a report concerning suction kits and catheters; Davol Products (undated).

(List continued on next page.)

Primary Examiner—Edgar S. Burr
Assistant Examiner—Eric P. Raciti
Attorney, Agent, or Firm—Lynn G. Foster

[57] ABSTRACT

An aspirating/ventilating or aspirating apparatus comprising multi-lumen catheter tubes, for evacuation of lung secretions and for other functions as well. Two and three lumen catheter tubes which comprise three unique distal catheter end structures are disclosed. Material comprising oxygen-containing gas is introduced into the lungs under positive pressure through a first lumen of the catheter tube at a predetermined rate while secretions (and gas) are simultaneously aspirated from the lung into a second lumen by force of negative pressure. Oxygen gas inflow is controlled to equal gas outflow to maintain the partial pressure of oxygen into the lung at a high respiratory level. In a first distal catheter end structure, an oxygen-containing gas is introduced through the first lumen as a circumscribing jet around the second lumen to provide fluid flow turbulence external to a second lumen to improve homogenization of localized secretions resulting in more efficient aspiration. In a second distal catheter end structure, oxygen gas inflow is introduced into a common chamber at the distal end of the catheter, where effluent secretions are being aspirated, causing gas produced homogenization in the turbulence created by influent/effluent flow at the common distal catheter entry/exit port. In a third distal catheter end structure in a three lumen catheter, provision is made for independent introduction of medication and/or lavage solutions into the lungs via a third lumen into a common entry/exit port. Provision is made for monitoring pressures and flow rates through the catheter tube.

39 Claims, 2 Drawing Sheets

U.S. PATENT DOCUMENTS

| | | | |
|---|---|---|---|
| 4,256,099 | 3/1981 | Dryden | 128/200.26 |
| 4,275,724 | 6/1981 | Behrstock | 604/281 |
| 4,300,550 | 11/1981 | Gandi et al. | 128/207.18 |
| 4,327,720 | 5/1982 | Bronson et al. | 128/207.15 |
| 4,426,062 | 1/1984 | Bowrom | 251/7 |
| 4,451,257 | 5/1984 | Atchley | 604/119 |
| 4,464,175 | 8/1984 | Altman et al. | 604/99 |
| 4,487,600 | 12/1984 | Brownlie | 604/35 |
| 4,569,344 | 2/1986 | Palmer | 128/207.16 |
| 4,573,965 | 3/1986 | Russo | 604/30 |
| 4,596,564 | 6/1986 | Spetzler | 604/281 |
| 4,613,323 | 9/1986 | Norton et al. | 604/43 |
| 4,637,389 | 1/1987 | Heyden | 128/207.15 |
| 4,638,539 | 1/1987 | Palmer | 128/207.16 |
| 4,652,255 | 3/1987 | Martinez | 604/27 |
| 4,676,778 | 6/1987 | Nelson, Jr. | 604/45 |
| 4,681,564 | 7/1987 | Landreneau | 604/97 |
| 4,696,296 | 9/1987 | Palmer | 128/207.16 |
| 4,735,606 | 4/1988 | Davison | 604/28 |
| 4,821,714 | 4/1989 | Smelser | 128/207.14 |
| 4,825,859 | 5/1989 | Lambert | 128/202.16 |
| 4,834,726 | 5/1989 | Lambert | 604/281 |
| 4,836,199 | 6/1989 | Palmer | 128/207.16 |
| 4,838,255 | 6/1989 | Lambert | 128/202.16 |
| 4,872,579 | 10/1989 | Palmer | 128/205.19 |
| 4,886,496 | 12/1989 | Conoscenti et al. | 604/96 |
| 4,938,741 | 7/1990 | Lambert | 604/19 |
| 4,946,440 | 8/1990 | Hall | 604/95 |
| 4,969,878 | 11/1990 | Schmidt et al. | 604/264 |

OTHER PUBLICATIONS

Superior Brochure "Continuous Ventilating Suction System" (undated).

Superior Advertisement "Infection Control Valve Suction Catheter" (undated).

Suctioning of left bronchial tree in the intubated adult, *Care Medicine,* Kamiaru; 092 (Date Unknown).

Evaluation of Selective Bronchial Suctioning Techniques Used for Infants and Children, Anesthesiology, 48:379–380 (date unknown).

Prevention of hypoxic Complication, 1968.

"Sterile suctioning with bare hands", The Nation's Hospitals & Diagnostic Laboratories, Fall 1975.

Comparison of Tracheobronchial Suction Catheters in Humans, *Chest,* vol. 69, pp. 179–181, Feb. 1976.

Selective tracheobronchial aspiration, *Thorax,* 32, 346–348, 1977.

Disposable Suction Catheter, *Nursing,* May 1979.

Evaluation of selective bronchial suctioning in the adult, *Critical Care Medicine,* vol. 8, No. 12, 1980.

MEDICAL ASPIRATING APPARATUS WITH MULTI-LUMEN CATHETER TUBE AND METHODS

1. Field of Invention

The present invention relates generally to aspiration of the lungs of a medical patient and, particularly, to a novel apparatus comprising a multi-lumen, multi-purpose catheter tube and more particularly to a novel distal end structure for multi-lumen, multi-purpose catheter tubes used primarily for removal of tracheobronchial secretions, and related methods.

2. Prior Art

Relevant, known prior art patents comprise U.S. Pat. Nos. 3,991,762 and 4,569,344. In each of these cases, an essentially linear single lumen catheter tube is provided, the sole purpose of which is insertion into and removal of secretions under negative pressure from the lungs of a medical patient. Difficulty is sometimes encountered in depleting the oxygen available to the patient in the lungs during secretion removal.

Multiple lumen prior art comprises U.S. Pat. No. 4,300,550 and an article published in Surgery, Vol. 63, No. 4, pgs. 586–587, April 1968, "Prevention of Hypoxic Complications during Endotracheal Suctioning." Both of these publications disclose a dual lumen catheter wherein one lumen is dedicated to aspiration and the other separate lumen to simultaneous oxygenation. Both publications deal restrictively with aspiration and concurrent oxygenation.

None of the prior art provides a way of stimulating removal of secretions which may not or do not respond to vacuum pressure alone. The addition of a lavage or medication or simultaneously providing a gas and lavage during secretion removal was not heretofore available.

In current medical treatment of a patient undergoing respiratory therapy, it is sometimes necessary to add fluids (lavage) to the lungs of the patients to dislodge and lubricate secretions. This is presently accomplished by delivering fluid to the opening of an indwelling endotracheal tube and allowing the fluid to run down the interior surface of the endotracheal tube. This method of lavage delivery is inefficient and ineffective because much of the fluid is blown back out of the tube when the patient coughs and a portion of the liquid is lost to evaporation before reaching the lungs. In addition, aspirated secretions sometimes lodge in the aspirating catheter during aspiration, reducing suctioning effectiveness, due to the size and thickness of aspirating secretions.

BRIEF SUMMARY AND OBJECTS OF THE PRESENT INVENTION

In brief summary, the present invention is intended to overcome or substantially alleviate the aforementioned limitations of the prior art and comprises either a novel ventilating/aspirating apparatus or a novel aspirating apparatus, the apparatus comprising a multi-lumen catheter tube with a unique distal end structure, for not only evacuation of lung secretions but for other significant functions as well. Accordingly, the present invention contemplates balancing the instantaneous gas volume in the lungs of a patient during evacuation of secretions therefrom by introducing material comprising oxygen-containing gas into the lungs under positive pressure through a first lumen of the catheter tube at one predetermined rate while secretions (and gas) are simultaneously removed through a second lumen by force of negative pressure. Optionally, at the same time medication or lavage solution may be introduced through the second or a third lumen of the catheter at a predetermined rate. Use of three lumens at the same time maintains the blood oxygen level of the patient within an acceptable range and simultaneously provides lavage solution, which may be unmodified until it flows out of the distal end of the catheter. It has been determined that introduction of gas under positive pressure from an aspirating catheter tube tends to agitate, loosen and homogenize lung secretions and that the delivery of gas at or in very close proximity to the aspirating orifice improves the effectiveness of aspiration. Furthermore, liquid medications and lavage solutions can be added to the lungs during secretion removal, as indicated, without evaporation or other modification of the liquid solutions, in a manner which provides lavage inside the lumen of the aspirating catheter as well as into the lung. Providing lavage solutions in this manner promotes more effective aspiration. Monitoring of gas flow rates and pressure may also be accommodated.

Accordingly, it is a primary object of the present invention to provide a novel aspirating apparatus, and related methods.

An important object of this invention is the provision of an aspirating apparatus comprising a novel catheter tube comprising a distal end which accommodates simultaneous flow or separate flow of any combination of material comprising gas, lavage and medications into the lungs of a patient and of gas and secretions removed therefrom.

A further significant object of the present invention is the provision of an aspirating apparatus comprising a novel multi-lumen, multi-purpose secretion removal catheter tube comprising multiple internal discharge orifices in the distal end of the catheter tube.

A further paramount object of the present invention is the provision of an aspirating apparatus and method which may be used to replenish lost effluent gas from the lungs of a medical patient during secretion evacuation with influent gas into the lungs.

A further valuable object of the present invention is the provision of an aspirating apparatus comprising a novel secretion removing multi-lumen catheter tube comprising a distal end which further comprises novel exit orifices by which influent fluids flow from a single catheter lumen to assist in introduction of lavage or the like into the lungs, and/or to dislodge and remove secretion from the respiratory system of a patient.

Another valuable object is the provision of a novel aspirating catheter tube accommodating simultaneous separate two-way flow to and from the lungs of a patient and, when and if desired, monitoring of flow rates and pressures.

A fundamental object of the present invention is provision of a multi-lumen catheter which comprises internal apertures for each lumen such that fluids delivered to the lung exit the catheter through the same orifice through which aspirated effluents flow.

A chief object of the present invention is introduction of lavage or other fluids into the distal end of a catheter without prior degradation comprising evaporation or mixing with other influents.

Another dominant object is the provision of a novel aspirating catheter tube for improved dislodgement and removal of secretions, introduction of lavage and the like and introduction of influent gas to compensate at least in part for aspirated gas.

These and other objects and features of the present invention will be apparent from the detailed description taken with reference to the accompanying drawings.

DETAILED DESCRIPTION OF THE ILLUSTRATED EMBODIMENTS

Removing secretions from the tracheobronchial tree is an integral part of the care given to patients who are intubated and receiving mechanical or other artificial ventilation. Secretions can be excessive in some respiratory disorders and constitute a serious threat to persons having such respiratory disorders. The presence of an endotracheal tube is a hindrance to the patient's efforts to clear secretions through natural coughing. Suction catheters are used to clear such secretions from the patient's airway.

The aspirating/ventilating apparatus disclosed in U.S. Pat. No. 4,569,344 is a device, which, among other things, is used to clear secretions from the lungs of a patient. This device is attached to the proximal, exposed end of the patient's indwelling endotracheal tube and is included as part of an overall ventilation circuit. A suction catheter is enclosed within a plastic bag to eliminate or minimize contamination thereof. As the patient requires artificial removal of secretions, the suction catheter advanced through a fitting of the ventilating device into the patient's airway and thence into a selected lung of the patient. Suction is thereafter applied to remove the secretions. Gas is also removed from the lung through the single lumen of the catheter tube as well as during aspiration of secretions The other lung may likewise be aspirated. Secretions are thus drawn into the lumen of the catheter tube and removed. The catheter tube is subsequently withdrawn into the plastic bag. The present invention is directed toward improved suction catheter tubes and intended to form a part of a ventilating/aspirating apparatus of the type disclosed in U.S. Pat. No. 4,569,344 or a part of an aspirating device which does not per se accommodate involuntary aspiration.

The present invention comprises a multi-lumen, multi-purpose two-way aspirating catheter tube comprising novel distal end structure and is intended to introduce material comprising oxygen-containing gas, into the lungs of a patient under positive pressure through one lumen of the aspirating catheter tube while secretions (and gas) are removed from the lungs under negative pressure through another lumen of the aspirating catheter tube.

The port by which gas delivered under pressure to the lungs is typically juxtaposed the entry port for secretions or enters into the distal end of the catheter near the entry port and is discharged from there. Thus, the influent gas under positive pressure tends to agitate, loosen and homogenize lung secretions, making removal thereof more efficacious. Providing an influx of oxygen gas while aspirating helps to maintain the blood oxygen level of the patient within an acceptable range. Liquid medications and lavage solutions may be added to the positive pressure influent through the gas carrying lumen or through a separate lumen which also is discharged into a single entry/exit port through which gas and other solutions exit and secretions are aspirated, as dictated by good medical practice. Monitoring of positive and negative pressure levels and flow rates is also accommodated.

Figure 1:
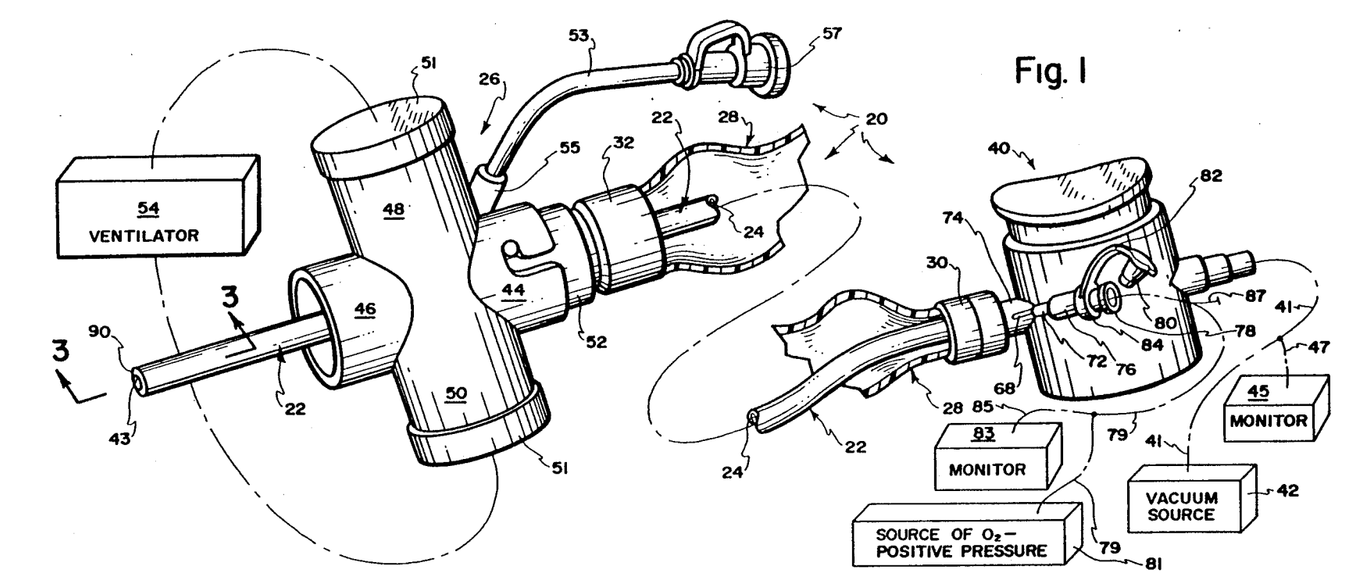
FIG. 1 is a perspective representation of a double lumen catheter ventilating/aspirating apparatus embodying the present invention.

Reference is now made to the drawings wherein like numerals are used to designate like parts throughout. A presently preferred integrated ventilator/aspirating mechanism, generally designated 20, is illustrated in FIG. 1 and embodies the principles of the present invention. It is to be appreciated, however, that the present invention applies equally to aspirating apparatus which lack involuntary ventilating capacity.

Ventilating/aspirating mechanism 20 is illustrated as capable of being connected to a medical patient by attachment of a tracheostomy connector 26 to the exposed end of an indwelling endotracheal tube. Mechanism 20 comprises a central portion comprising an internal aspirating catheter tube 22 having a first hollow interior passageway or lumen 24 (FIGS. 2-6) of sufficient capacity to aspirate secretions from the trachea and bronchi under force of negative pressure. The catheter tube 22 also comprises at least one hollow interior passageway or lumen 25 (FIGS. 2-6) which delivers gas under positive pressure to the lungs of the patient during secretion evacuation and solutions comprising lavage or medications. The aspirating catheter tube 22 is formed of a suitable synthetic resinous material which is yieldable but shape-retaining when in an unstressed condition, such as medical grade transparent polyvinyl chloride. It may be extruded. The outside diameter of the catheter tube 22 is selected to comfortably pass loosely through the endotracheal tube and into either lung of the patient and the wall thickness is selected to avoid occlusion of any lumen due to kinking or the like.

The aspirating catheter tube 22, therefore, has sufficient strength to prevent buckling, bending and twisting of the catheter tube, which would otherwise occlude or tend to occlude the interior passageways of the catheter tube. In the assembled condition, the tube 22 is illustrated as being surrounded in substantially sealed relation by a sack or flexible collapsible envelope 28, formed of suitable impervious synthetic resinous film material of medical grade, such as polyethylene film in sleeve form.

The flexible envelope 28 is selectively attachable and detachable at each end, as explained herein, allowing ready manual manipulation of the Catheter tube 22 by gripping action on the part of the user applied to the exterior of the envelope 28. The catheter tube 22 is preferably controlled solely by manual manipulation thereof through the envelope.

The flexible envelope 28 is held by an interference fit at the opposite ends thereof using collars 30 and 32, respectively. See FIG. 1. The interference fit couplings 30 and 32 together with an aspirating vacuum controlled valve 40 and the tracheostomy tube connector 26 are illustrated as being of known components. These components are described in substantial detail in U.S. Pat. No. 4,569,344, the content of which is incorporated herein by reference for purposes of simplifying this detailed description. It should be noted, however, that the aspirating lumen 24 of the catheter tube 22 is in fluid communication with the distal side of the valve 40. The proximal side of the valve 40 in turn is in fluid communication via line 41 with a vacuum source 42, such as a conventional hospital suction system. A pressure and flow rate monitor 45 is illustrated as being connected to line 41 via line 47.

In short, when the catheter tube 22 is in the appropriate indwelling position in the lung of a medical patient, the valve 40 is manually actuated so that the vacuum of source 42 is applied to the aspirating lumen 24 of the catheter tube 22 thereby causing undesired secretions accumulated in the lung to enter the catheter tube 25 through the tip opening or influent port 43 and to flow along the lumen 24 of the catheter tube 22.

The connector 26 is illustrated as being in the form of a cross fitting. The fitting 26 provides an external seal against a loss of air or liquid pressures applied to a lung of a patient but accommodates snug slidable displacement of the catheter tube 22 through the fitting 26. The fitting 26 comprises first, second, third and fourth port structure 44, 46, 48 and 50. Ports 48 and 50 are illustrated as being closed by removable caps 51. Port structure 44 releasibly connects through a fitting 52 to the distal end of the plastic envelope 28. Port structure 46 is appropriately fitting upon an exposed end of an indwelling endotracheal tube, while port structure 48 and 50, respectively, with the caps 51 removed, connect to the output and exhaust terminals of a conventional ventilator 54 for involuntary ventilation of the patient. Thus, ventilator 54 drives air through either port 48 or 50 into the respiratory system of the patient via port 46 under positive pressure and evacuates gases from the respiratory system of the patient via port 46 through the other port 50 or 48 to the ventilator 54.

Connector 26 also comprises a hollow irrigation tube 53 joined to the housing of connector 26 at hollow fitting 55. During periods of non-use, irrigation tube 53 is closed, at its distal end by a removable tethered cap 57. Irrigation tube 53 is used to deliver an irrigation solution to catheter tube 22 to remove secretions from the interior and exterior thereof during and after withdrawal of the catheter tube from the respiratory system of a patient. The specific structure and exact function of the irrigation tube and related parts are set forth in U.S. Pat. No. 4,569,344, to which reference may be made.

In the past, it has been the state-of-the-art to utilize aspirating catheter tubes solely for the purpose of subjecting the interior thereof to negative pressure, thereby withdrawing undesired secretions from the lungs of a medical patient and more recently to use multi-lumen catheters for the purpose of supplying oxygen while aspirating to maintain adequate oxygen blood levels during aspiration. However, sometimes the lung secretions, which accumulate over a period of time (typically in the course of involuntary respiration), are resistant to evacuation under a reasonable level of vacuum pressure. In the course of making the present invention, it has been learned that agitation, homogenation and a displacement of such secretions under positive pressure will facilitate the evacuation of the same under negative pressure and will maintain the blood oxygen level of the patient within acceptable limits. It is also sometimes desirable to add one or more liquid medications and/or lavage solutions to the lungs for purposes comprising promoting improvements in aspiration and/or ventilation.

The present invention, for the first time, provides a multi-lumen, multi-purpose aspirating catheter tube with novel distal end structure, which can be used in conjunction with the aspirating/ventilating apparatus illustrated in FIG. 1, any comparable ventilating/aspirating apparatus, and in conjunction with an aspirating apparatus which does not provide capacity for causing a medical patient to involuntarily respirate.

Figure 2:
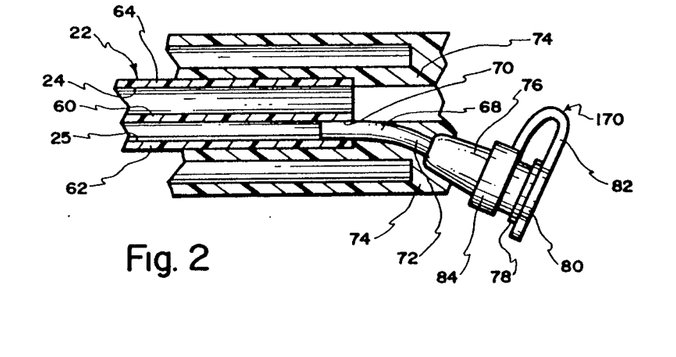
FIG. 2 is an enlarged fragmentary longitudinal cross-section of the proximal end of the double-lumen catheter tube of FIG. 1.
Figure 3:
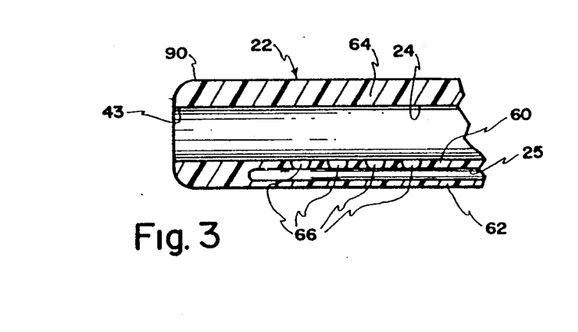
FIG. 3 an enlarged fragmentary cross-section of the distal end of the double-lumen catheter of FIG. 1 taken along lines 3—3 of FIG. 1.
Figure 4:
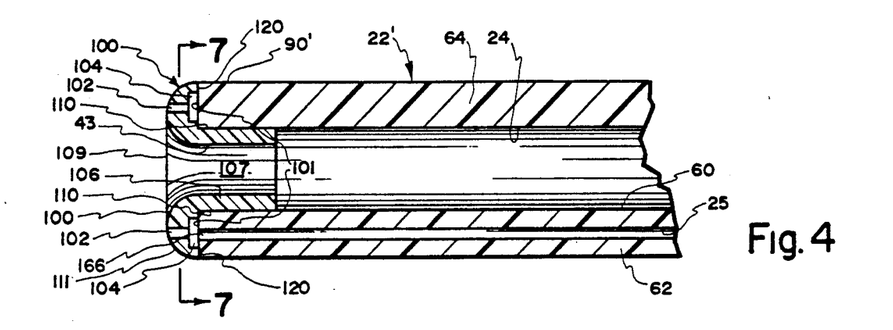
FIG. 4 is an enlarged fragmentary cross-section similar to FIG. 3 but of the distal end of another double-lumen catheter fabricated according to the present invention, which comprises an irrigator distal end tip.
Figure 5:
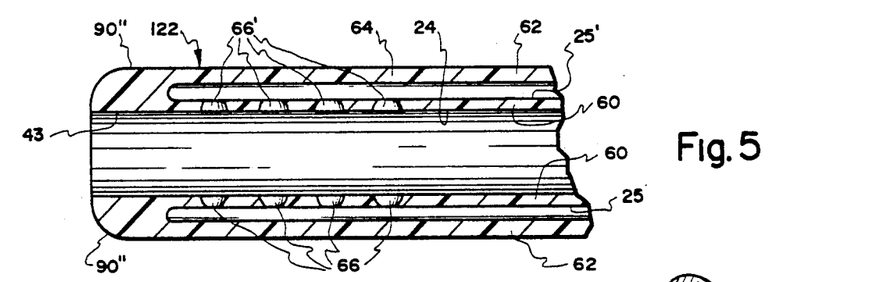
FIG. 5 is an enlarged fragmentary cross-section similar to FIG. 3; of the distal end of a triple-lumen catheter.
Figures 6, 7:
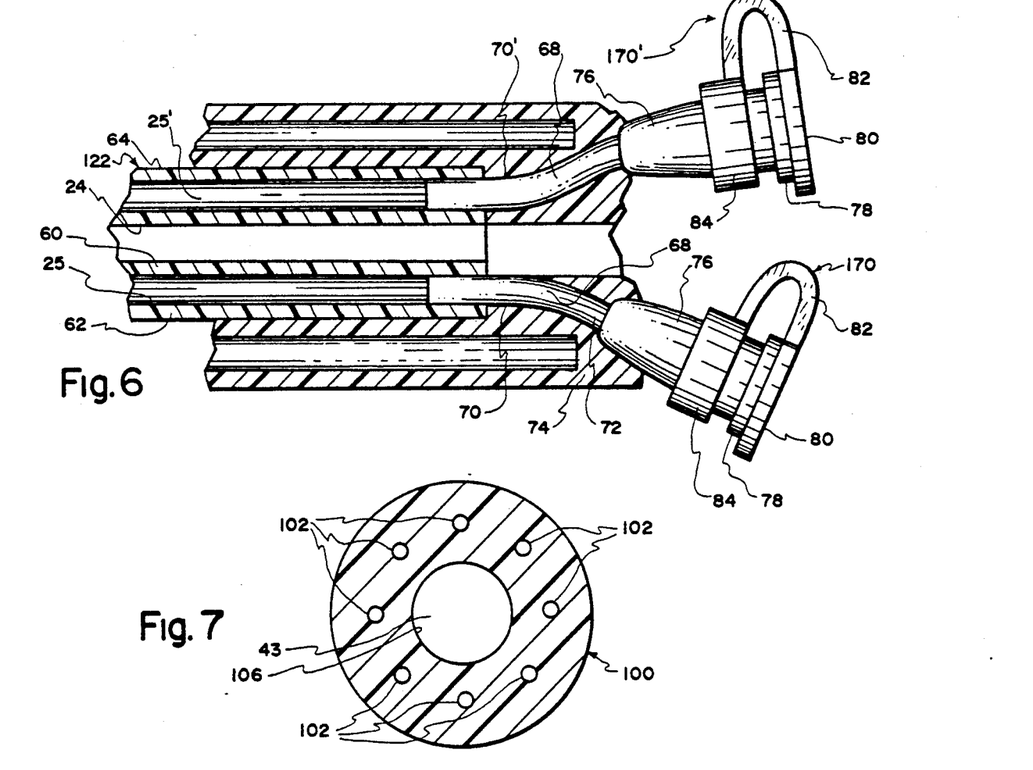
FIG. 6 is an enlarged fragmentary longitudinal cross-section similar to FIG. 2 of the proximal end of a triple lumen catheter tube fabricated according to the present invention.
FIG. 7 is a cross-section along lines 7—7 of FIG. 4.

With specific reference once more to the drawings, it is shown in FIGS. 2-6 that catheter tubes 22 and 122 each comprise not only an aspirating lumen 24, which is subjected to negative pressure from the vacuum source 42 across manually-operable valve 40, but a second lumen 25 which provides a channel for oxygen under positive pressure to the lung. As well, catheter tube 122 comprises a third lumen 25' which provides a channel for delivery of lavage solution and/or medication to the lung, as shown in FIGS. 5 and 6. In FIG. 2, second lumen 25 is shown separated from the aspirating lumen 24 by an interior wall 60, which has sufficient structural rigidity and integrity to prevent occlusion of either lumen 24 or 25. Preferably, as stated earlier, the catheter tube 22 is formed as one piece, such as by use of conventional extrusion techniques. The second lumen 25 is also defined by a limited segment 62 of the exterior wall 64. It is the intent of the present invention to utilize the second lumen 25 to displace material comprising a gas containing oxygen along the length thereof and deliver the same, typically on a continuous basis, to the lungs of the patient, with the catheter tube 22 inserted therein, simultaneous with the evacuation of secretions under negative pressure via lumen 24. This typically occurs, when an aspirating/ventilating apparatus is involved, such as that shown in FIG. 1.

Accordingly, the influent material comprising gas under positive pressure, displaced into the proximal end to flow from the distal end of the second lumen 25 through ports, nozzles, or orifices 66, enters the respiratory system of the patient through effluent port 43. See FIG. 3. Ports 66 are closely juxtaposed the aspirating port 43, creating bi-directional counter fluid flow in the distal tip region 90 of the catheter tube 22. The orifices 66 open inwardly into the aspirating lumen 24 so that the counter flows are fluidically contiguous. Discharge from nozzles 66 is in the nature of a spray independent of whether the fluid discharged is gaseous, liquid or both. The proximal end of the second lumen 25 is in communication with a hollow elbow 68 of proximal communicating apparatus 170, whiCh is telescopically secured at its forward end within the hollow of the lumen 25, contiguously at site 70. A suitable adhesive or bonding agent may be utilized at site 70 to prevent inadvertent separation of the elbow 68 from the proximal end of the lumen 25. The elbow 68 is illustrated as turning through approximately 45 and may be formed of any suitable material in such a way as to prevent occlusion and to accommodate flow through the hollow interior thereof of the influent material under positive pressure to the lungs as mentioned earlier.

The trailing end 72 of the elbow 68 is shown as to have passed through the distal cantilevered projection 74 to the exterior of the device. Thus, &railing end 72 is exposed and is integrally joined to a hub 76. Hub 76 comprises a conventional luer loc fitting 78 at the extreme trailing end thereof, by which a pressure line 79 may be releasibly coupled for introduction of gas comprising oxygen under positive pressure into the lumen 25. Pressure line 79 connects to a source 81 of oxygen-containing gas under positive pressure. A monitor 83 for measuring pressures and flow is illustrated as being connected to line 79 via line 85. Medications and/or lavage solution may be conventionally added at tee 87 to the materials displaced along lumen 25 for delivery to the respiratory system of the patient.

The hub 76 is hollow and in aligned fluid communication with the hollow interior of the elbow 68. During times of nonuse, the interior of the hub 76 at the trailing end thereof is closed by an elastomeric press-fit cap 80, with the line 79 disconnected and source 81 off. When the plug 80 is open, it is held to the exterior of the hub 76 by a tether 82, which is integral with a collar 84. Collar 84 snugly surrounds or encircles the exterior of the hub 76 adjacent the luer loc flange 78.

Gas, ordinarily containing a high percentage of oxygen, is introduced during secretion removal along the fluid path defined seriatim by the source 81, line 79, the hollow interior of hub 76, the hollow interior of the elbow 68, the lumen 25 and the ports 66 in distal catheter end 90. The gas is introduced at sufficiently high pressure that the gas velocity carries the major proportions of said gas outward from port 43 where the oxygen contained therein provides a higher oxygen partial pressure in the vicinity of the distal end of catheter 22. During aspiration of secretions, the quantity of gas displaced into the lungs via lumen 25 is preferably balanced or nearly so as against the amount of gas removed along with the secretions from the respiratory system of the patient via lumen 24. Thus, the simultaneous influent turbulent gaseous flow occurring out of port 43 of the catheter tube 22 as effluent flow is simultaneously drawn through the same lumen of the catheter tube 22, in the form of both gas and secretions causes the secretions to homogenize for more effective aspiration. The agitation and homogenation of the secretions within the respiratory system of the patient by reason of the mild turbulence of the influent gas loosens and mixes the secretions and increases the secretion volume available for evacuation, leaving the lungs with a greater respiratory capacity thereafter. Also, this maintains the respiratory oxygen level within an acceptable range.

A second presently preferred embodiment is shown in FIG. 4, wherein a distal end 90' of a catheter tube 22' comprises a different effluent port structure for servicing the lungs from second lumen 25. Catheter tube 22' is preferably formed as one piece, such as by use of conventional extrusion techniques. However, at distal catheter end 90', a multiple nozzle annular spray end attachment, generally designated 100, is added to circumferentially provide distributed high velocity fluid flow adjacent to port 43. Second lumen 25 ends distally at port 166 disposed at blunt distal edge 101 of catheter tube wall 64 where exiting fluid enters catheter end attachment 100 reservoir into annular chamber or plenum 104 to flow into the lung cavity through multiple nozzle ports 102. The circumferential distribution of ports 102 is shown in FIG. 7.

End attachment 100 comprises an annular projection 106 and a base portion 111, in which chamber or plenum 104 and nozzles 102 are formed perpendicular to annular planar surfaces 110 and 120 which are respectively adhesively bonded to tube edge 101 and the interior surface 24 of catheter tube 22. Surface 120 is centrally recessed to form plenum 104, which opens first to receive flow from port 166 of the second lumen 25 and second to communicate said flow to the series of nozzle ports 102. Internally projecting annular projection 106 of attachment 100 snugly fits into distal catheter end 90' so as to be non-occlusive of attachment 100. Projection 106 comprises internal surface 107 which integrally merges into exposed arcuate surface 109 of base 111.

End attachment 100 is preferably made from suitable synthetic resinous material, which can be adhesively bonded to catheter tube 22'. The maximum external diameter of end attachment 100 at base 111 is illustrated as being essentially the same as catheter tube 22' and hole diameter, for each of the eight orifice spray nozzle ports 102 shown in FIG. 7, is preferably approximately one third the diameter of second lumen 25. When the effluent issuing from port 166 is oxygen gas, the gaseous spray tends to dislodge, mix and/or homogenize the aspirant near catheter end 90' for more effective and efficient suctioning.

Another presently preferred catheter embodiment is seen in FIGS. 5 and 6, wherein many of the catheter ports and lumens have the same or similar form and the same or similar function as those of catheter tube 22. Where form and function are the same, like numbers are used and further description is not necessary. In this embodiment, a catheter tube 122 comprises two eccentric side wall catheter lumens 25 and 25' in addition to central aspirating lumen 24, which is subjected to negative pressure from vacuum source 42 across the manually-operable valve 40, when the distal end of catheter 122 is appropriately positioned in the lung of a patient. Second lumen 25 and third lumen 25' are identically though oppositely configured, but in spaced, separate areas of exterior wall 64, in catheter 122. The configuration of second lumen 25 is the same, or substantially the same, as earlier described in conjunction with catheter tube 22 including internal distal end ports 66.

Third lumen 25' comprises communicating ports 66' which are preferably identical or substantially identical to ports 66 of second lumen 25, but oppositely disposed and oppositely directed. Thus, distal end 90" of catheter tube 122 comprises entry capability for simultaneous or sequential delivery to the lungs of a patient of two separate fluids. Such capability enhances aspirating catheter performance by dislodgement and homogenization of aspirated secretions, as earlier described, and by delivering a fraction of lavage solution or liquid medication under positive pressure through lumens 25 or 25' to the distal end 90" of the catheter tube 122 to lubricate and aid the flow of aspirated secretions and to add a medicinal benefit. The unaspirated fraction of injected lavage solution flows out of port 43 to act upon nearby biological material due to the egressing velocity of the lavage.

The effect upon the patient of oxygen influent into the respirating system and aspiration effectiveness and efficiency is the same or substantially the same for catheter 122 as earlier described for catheter 22. Similarly, the proximal communicating apparatus 170 for lumen 25 is the same as earlier described. However, in the three lumen catheter tube 122, a second identical proximal end communicating apparatus 170' is illustrated as being connected at the proximal end of third lumen 25' with a second hollow elbow 68, which is telescopically secured at its forward end within the hollow end of lumen 25', contiguous at site 70' to preVent inadvertent separation of second elbow 68 from the proximal end of lumen 25'. Second elbow 68 also turns through 45 degrees, but in an opposite direction to first elbow 68, to provide non-competitive access to each proximal end communicating apparatus 170 and 170'. Materials used in construction and functionality of proximal end communication apparatus 170' are the same as those of proximal end communicating apparatus 170, except that proximal end communicating apparatus 170' is joined to lumen 25' rather than lumen 25.

The provision for two influent lumens allows addition of lavage and medication independent of oxygen being supplied, both of which can be controlled and provided independently from but simultaneous or sequential in respect to aspiration of secretions through valve 40. It is within the scope of this invention to add lumens and proximal end communicating apparatus for additional independent influent medicative paths.

In current use, the triple lumen catheter 122 of FIGS. 5 and 6 may introduce gas during secretion removal, for example, along the fluid path defined seriatim by the source 81, line 79, and connections to proximal communicating apparatus 170 comprising the hollow end of first hub 76, the hollow interior of first elbow 68, the lumen and the ports 66, as shown in FIG. 1 and earlier described. Lavage solution or medications may be delivered independently, for example, through proximal end communication apparatus 170' by connecting a syringe or other positive pressure source for lavage or medicant to proximal end communication apparatus 170' comprising the hollow interior of second hub 76, the hollow interior of second elbow 68, the lumen 25' and ports 66'. This connection allows independent distribution of lavage and medicant to the distal end 90" of catheter 122 as determined necessary by an operating technician. The high velocity of influent through ports 66' combines with the turbulent flow of fluid from ports 66 to improve the effectiveness and efficiency of lung aspiration.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. An aspirating apparatus for respiratory therapy in a human lung comprising:
    proximal end means comprising first site means further comprising means for selectively communicating a negative fluid pressure to and within the lung and second site means further comprising means for selectively communicating a positive pressure gas flow to and within the lung;
    a multi-purpose lung receiving aspirating catheter tube for respiratory therapy comprising secretion aspirating lumen means;
    the apparatus comprising first fluid communication means by which the aspirating lumen mean are placed in fluid communication with the negative fluid pressure communicating means;
    the aspirating lumen means comprising distal end entry port means by which secretions and gas from the lungs of a patient enter the aspirating lumen means under force of negative pressure;
    the multi-purpose aspirating catheter tube for further comprising second lumen means;
    the apparatus comprising second fluid communication means by which the second lumen means are placed in fluid communication with positive pressure gas;
    the second lumen means comprising distal end effluent port means by which the gas under force of the positive pressure is introduced to and within the lungs of the patient;
    the distal end effluent port means being closely juxtaposed the distal end entry port means whereby at least partial intermixing flow within a common region adjacent to the distal tip of the catheter tube is accommodated.

2. An aspirating apparatus according to claim 1 wherein the effluent port means comprise a plurality of effluent orifices open inwardly into the aspirating lumen means at the distal end of the catheter tube where said common region is located.

3. An aspirating apparatus according to claim 1 wherein the effluent port means comprise a plurality of effluent orifices open generally parallel to but offset from the longitudinal axis of the catheter tube and the common region is disposed beyond the entry port means.

4. An aspirating apparatus according to claim 1 wherein the effluent port means comprise a plurality of effluent orifices in the nature of an annular array of discharge nozzles circumscribing the distal end of the aspirating catheter tube wherefrom fluid is emitted coaxially with respect to the distal end of the entry port means to agitate and homogenize lung secretions for more efficient and effective aspiration.

5. An aspirating apparatus according to claim 1 wherein the first site means comprise manually operable valve means.

6. An aspirating apparatus according to claim 1 wherein the second fluid communication means comprise hollow tubular means and proximal hub means whereby accessible connection is made between a source of gas for delivery at the positive pressure and the second lumen means.

7. An aspirating apparatus according to claim 1 wherein the aspirating catheter tube is formed from synthetic resinous materials as one piece.

8. An aspirating apparatus according to claim 1 further comprising means for monitoring pressures and flow rates through the catheter tube.

9. A method of selectively removing secretions from the lungs of a patient undergoing respiratory therapy, comprising the steps of:
    inserting a multi-lumen aspirating catheter tube into a lung site within the respiratory system of a patient;
    applying negative pressure to one lumen of the aspirating catheter tube and thence to the lung to thereby evacuate secretions and gas from the lungs of the patient to a distal port of the aspirating catheter tube and delivering oxygen-containing gas through a second lumen of the aspirating catheter tube to and directly within a lung so as to at least partially bi-directionally commingle the evacuation flow and the oxygen-containing gas flow at a common region within the lung in the vicinity of the distal end of the aspirating catheter tube.

10. A method according to claim 9 wherein the oxygen-containing gas compensates for loss of gas due to secretion removal.

11. A method according to claim 9 further comprising the step of delivery of liquid medication with the oxygen-containing gas.

12. A method according to claim 9 further comprising the step of delivery of lavage solution with the oxygen-containing gas.

13. An aspirating apparatus for respiratory therapy comprising:
proximal end means comprising first site means comprising means for selectively communicating a negative pressure and second site means further comprising means for selectively communicating a fluid under positive pressure;
a multi-purpose lung receiving aspirating catheter tube for respiratory therapy comprising first secretion aspirating lumen means, second gas delivery lumen means, and distal end means;
first fluid communication means by which the aspirating lumen means are placed in fluid communication with the negative pressure of the communicating means;
second fluid communication means by which the second influent gas delivering lumen means under positive pressure are placed in fluid communication with the positive fluid pressure communicating means;
the distal end means comprising entry port means in fluid communication with the aspirating lumen means by which effluent secretions and effluent gas from the lungs of a patient enter the aspirating lumen means under force of negative pressure from the negative pressure communicating means and gas discharge port means in fluid communication with the second lumen means by which gas is discharged into a desired lung location of a patient under force of positive pressure from the positive pressure communicating means, the discharge port means comprising an array of nozzle means located and directed so as to deliver said influent gas to a region at or near the distal end of the aspirating catheter tube where the effluent secretion and gas flow also occurs which create a contiguous turbulence between said influent and effluent flows.

14. An aspirating apparatus according to claim 13 wherein the first site means comprise manually operable valve means.

15. An aspirating apparatus according to claim 13 wherein the second fluid communication means comprise accessible hollow tubular means and proximal hub means whereby facile connection exists between the second lumen means and the second site means.

16. An aspirating apparatus according to claim 13 wherein the catheter tube is formed from synthetic resinous materials as one piece.

17. An aspirating apparatus according to claim 13 further comprising means for monitoring pressures and flow rates through the catheter tube.

18. A method for selectively removing secretions from the lungs of a patient undergoing respiratory therapy, comprising the steps of:

inserting a multi-lumen aspirating catheter tube into a lung site within the respiratory system of a patient;
applying negative pressure to a first lumen of the aspirating catheter tube to thereby evacuate secretions and gas from the lung site into the distal end and thence along the first lumen of the catheter and at the same time delivering lung influent fluid through a second lumen of the aspirating catheter tube and out a plurality of nozzles disposed at the distal end of the aspirating catheter tube into the lungs of the patient after at least turbulently engaging at the distal end of the catheter tube the flow of secretions and gas being evacuated.

19. A method according to claim 18 wherein the lung influent fluid comprises oxygen-containing gas to compensate for loss of oxygen with the evacuation of secretions.

20. A method according to claim 18 wherein the lung influent fluid comprises oxygen-containing gas delivered in such a way as to agitate and stimulate secretion evacuation.

21. A method according to claim 18 wherein the lung influent fluid comprises liquid medication.

22. A method according to claim 18 wherein the lung influent fluid comprises lavage solution.

23. An aspirating apparatus for respiratory therapy containing:
proximal end means comprising first site means further comprising means for selectively delivering negative fluid pressure, second site means further comprising means for selectively and independently delivering positive fluid pressure, and third site means further comprising means for selectively and independently delivering positive fluid pressure;
a multi-purpose catheter tube for respiratory therapy comprising first secretion aspirating lumen means comprising first inner wall means; second lumen means comprising second inner wall means, at least third lumen means comprising third inner wall means, and distal end means;
first fluid communication means by which the aspirating lumen means are placed in fluid communication with negative fluid pressure delivering means;
second fluid communication means by which the second lumen means are placed in fluid communication with second site means positive fluid pressure delivering means;
third fluid communication means by which the third lumen means are placed in fluid communication with third site means positive fluid pressure delivering means;
the distal end means comprising distal entry port means in fluid communication with the aspirating lumen means by which secretions and gas from the lungs of a patient enter the aspirating lumen means under force of negative pressure from the negative fluid pressure delivering means and (a) first discharge port means providing fluid communication through the first and second inner wall means proximal to the distal entry port means wherefrom fluid is discharged into a desired lung location of a patient under force of positive pressure from the second site means positive fluid pressure delivering means and (b) second discharge port means providing fluid communication through the first and third inner wall means proximal to the distal entry port means by which fluid is also discharged into a desired lung location of a patient under force of positive pressure from the third site means positive fluid pressure delivering means.

24. An aspirating apparatus according to claim 23 wherein the first site means comprise manually operable valve means.

25. An aspirating apparatus according to claim 23 wherein the second and third communication means each comprise accessible catheter hollow tubular means and proximal hub means whereby facile connection is made between the second and third lumen means and the second and third site means, respectively.

26. An aspirating apparatus according to claim 23 wherein the catheter tube is formed from synthetic resinous materials as one piece comprising the aspirating lumen means, the second lumen means, third lumen means and wall means circumscribing the aspirating, second and third lumen means.

27. An aspirating apparatus according to claim 23 further comprising means for monitoring pressures and flow rates through the catheter tube.

28. A method of selectively removing secretions from the lungs of a patient undergoing respiratory therapy, comprising the steps of:
  inserting a multi-lumen catheter tube, comprising an orifice at the distal end thereof, into a lung site within the respiratory system of a patient;
  applying negative pressure to a first lumen of the catheter tube to thereby evacuate effluent secretions and gas from the lungs of the patient proximally through the orifice, selectively delivering fluid through a second lumen of the catheter tube and into the lung site from a first port means proximal to the orifice and therefrom distally through the orifice and selectively and independently delivering fluid through a third lumen of the catheter tube and into the lung site from second port means proximal to the orifice and therefrom distally through the orifice.

29. A method according to claim 28 wherein the fluid from one of the port means comprises oxygen.

30. A method according to claim 28 wherein the fluid from one of the port means comprises a therapeutic liquid.

31. A method according to claim 29 wherein the oxygen at least partially compensates for evacuated gas.

32. A method according to claim 28 wherein the fluid delivered to the lung site agitates and stimulates secretion removal and evacuation.

33. A method according to claim 30 wherein the liquid comprises medication.

34. A method according to claim 30 wherein the liquid comprises lavage.

35. An aspirating apparatus for respiratory therapy comprising:
  proximal end means comprising first site means further comprising means for selectively delivering a negative fluid pressure and second site means further comprising means for selectively delivering a positive fluid pressure;
  a multi-purpose catheter tube for respiratory therapy comprising secretion aspirating lumen means which further comprise first inner wall means;
  the apparatus comprising first fluid communication means by which the aspirating lumen means are placed in fluid communication with the negative fluid pressure delivering means;
  the aspirating lumen means comprising distal end entry port means by which secretions and gas from the lungs of a patient enter the aspirating lumen means under force of negative pressure from the negative pressure delivering means;
  the multi-purpose catheter tube for respiratory therapy further comprising second lumen means which further comprise second inner wall means;
  the apparatus comprising second fluid communication means by which the second lumen means are placed in fluid communication with the positive fluid pressure delivering means;
  the second lumen means comprising distal end effluent port means by which fluid material under force of the positive pressure is introduced into the lungs of the patient;
  the distal end effluent port means being closely juxtaposed the distal end entry port means and comprising a plurality of spaced effluent orifices proximal to the entry port means which communicate between the first and second inner wall means whereby bi-directional counter flow at the distal tip of the catheter tube is accommodated.

36. An aspirating apparatus according to claim 35 wherein the first site means comprise manually operable valve means.

37. An aspirating apparatus according to claim 35 wherein the second fluid communication means comprise hollow tubular means and proximal hub means whereby accessible connection is made between the positive pressure delivery means and the second lumen means.

38. An aspirating apparatus according to claim 35 wherein the catheter tube is formed from synthetic resinous materials as one piece comprising the aspirating lumen means, the second lumen means and wall means circumscribing both lumen means.

39. An aspirating apparatus according to claim 35 further comprising means for monitoring pressures and flow rates through the catheter tube.

* * * * *